United States Patent
Wetzig et al.

(10) Patent No.: US 6,350,263 B1
(45) Date of Patent: Feb. 26, 2002

(54) ABLATING ARRANGEMENT

(75) Inventors: Thomas Wetzig, Munich; Markus Graf, Berlin; Steffen Sachse, Dresden; Olaf Pohl, Pirna, all of (DE)

(73) Assignee: Biotronik Mess- und Therapiegeräte GmbH & Co. Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/291,331

(22) Filed: Apr. 15, 1999

(30) Foreign Application Priority Data

Apr. 15, 1998 (DE) ......................... 198 17 553

(51) Int. Cl.⁷ ............................................. A61B 18/14
(52) U.S. Cl. ..................... 606/41; 606/34; 600/374; 600/393; 607/99; 607/113
(58) Field of Search ................... 600/374, 393; 606/41, 34, 10–12; 607/99, 113

(56) References Cited

U.S. PATENT DOCUMENTS

| | | |
|---|---|---|
| 5,462,544 A | 10/1995 | Saksena et al. |
| 5,570,218 A | 10/1996 | Sotom |
| 5,584,830 A | 12/1996 | Ladd et al. |
| 5,722,401 A | 3/1998 | Pietroski et al. |

FOREIGN PATENT DOCUMENTS

| | | |
|---|---|---|
| DE | 9016985 | 4/1991 |
| EP | 0732079 | 9/1996 |
| WO | WO 96/00036 | 1/1996 |
| WO | WO 96/00039 | 1/1996 |
| WO | WO 97/20510 | 6/1996 |
| WO | WO 96/32885 | 10/1996 |
| WO | 97/33526 | 9/1997 |

OTHER PUBLICATIONS

Microprocessor, Special Edition Magazine *Electronic*, Franzis Publishing, Munich, "Analog Input/Output Systems for Microcomputer", 1977, p. 104.

*Primary Examiner*—Lee Cohen
(74) *Attorney, Agent, or Firm*—Venable; Robert Kinberg; Catherine M. Voorhees

(57) ABSTRACT

An ablation arrangement (1) for the targeted production of local lesions in living tissue inside the body, particularly inside the heart, comprising at least one energy source (15), a plurality of energy uncoupling elements (11b to 11g) that are attached to a holding element (11a), a plurality of energy transmission lines (19.1) that connect the energy source or the energy sources to the energy uncoupling elements and switching elements (9.3) that are assigned to the energy transmission lines for setting up or interrupting a connection between the energy source and respectively one energy uncoupling element, with program control means (9.1) for a time-sequential actuation of at least some of the switching elements according to an ablation program.

18 Claims, 3 Drawing Sheets

ABLATING ARRANGEMENT

BACKGROUND OF THE INVENTION

The invention relates to an ablating arrangement for the targeted production of local lesions in living tissue inside a body, particularly in a heart, comprising: at least one energy source; a holding element; a plurality of energy uncoupling elements mounted on the holding element; a plurality of energy transmission lines connecting the at least one energy source to the energy transmission lines for one of activating and interrupting a connection between the at least one energy source and respectively one energy uncoupling element.

Such ablating arrangements are known and have proven themselves in clinical applications. The energy source (e.g. a HF generator and amplifier) can be connected to different electrodes of a multi-polar catheter through manually operated switches, so as to achieve a lesion pattern desired by the doctor.

These manually operated arrangements are very flexible with respect to use, but are difficult to operate.

Another type of ablation arrangement is known from the international patent application WO-A-97/20510. The HF ablation system, described therein, can be used to release HF energy simultaneously and with predetermined phase coordination via several electrodes of a multi-polar catheter. The number of power modules used for this corresponds to the number of electrodes.

The last-named arrangement is structurally very involved and expensive. Also, the various electrode systems are not mutually uncoupled, so that measuring circuits and control circuits, based thereon, influence each other. It is therefore the object of the invention to specify a cost-effective and easy to operate ablation arrangement.

SUMMARY OF THE INVENTION

This object is solved with an ablation arrangement of the type first mentioned above and further comprising program control means, including a program memory storing a control program, for performing a time-sequential actuation of at least some of the switching elements according to the control program.

The invention includes the idea of automating the ablation to such a degree that a mode for connecting the energy source to the individual uncoupling elements for introducing energy at predetermined locations to the tissue can be determined ahead of time and individually, and can subsequently be realized quickly and in a timely fashion with an automatic sequence. The physician is thus relieved of having to activate switches continuously during an operation while not being restricted in his/her freedom to position the lesion regions according to the concrete findings. On the contrary, the physician can focus more attention on the patient or the positioning of the catheter. By shortening the ablation procedure, the risks of radiation stress and an incorrect positioning of the catheter are reduced.

For this purpose, one advantageous modification of the invention provides an ablation program memory, having a number of storage regions that correspond to the number of energy output elements, as well as means for influencing an ablation program stored in the ablation program memory in dependence on at least one variable, which is input prior to or during the treatment and/or is measured during the treatment. Thus, while the basic mode of sequentially connecting the individual uncoupling locations with the energy source is determined ahead of time, there are degrees of freedom—in addition to the also existing options for an emergency shut-down—above all with respect to the concrete or pre-programmed time-dependent sequence and particularly for taking into account actually obtained measuring values, which reflect the status of the treatment.

One of the preferred embodiments of the HF ablation arrangement provides that the energy source is designed as an HF voltage source (with corresponding amplifier), the holding element as a catheter body, the energy uncoupling elements are designed as electrodes, the energy transmission lines as electrical lines (these parts together form a multipolar ablation catheter, known per se), and the switching elements as electromechanical or electronic switches.

The energy source as well as various ablation catheters for use with the invention are known per se and do not need to be described in further detail here. Relays or semiconductor switches, for example, can be used as switching elements (these are preferred in CMOS technology). The invention makes it possible to essentially simplify the device technologically and reduce costs by using only a single energy-source for the multiplex operation, specifically a single HF amplifier. Owing to the option of a synchronous switching of the HF line and temperature measuring points, several temperature control circuits can be operated, which do not interfere with each other.

In principle, the invention can also be used with different types of ablation arrangements, for example if the energy source is designed as an high-power radiation source, particularly a laser source, the holding element as a catheter body, the energy transmission lines and the energy uncoupling elements are designed as a waveguide arrangement and the switching elements are designed as electro-optical switching elements.

In favorable embodiments, the energy uncoupling elements simultaneously serve as sensors. A measuring signal processing unit for evaluating the recorded measuring signals is provided, which can be additionally connected to the energy transmission lines. The individual energy uncoupling elements in this case are switched by the program control means to the input of the first measuring signal processing unit by way of the switching elements.

In a preferred HF ablation arrangement, the electrodes are designed to pick up in particular intracardiac electrogram signals, including monophase action potentials (MAP). The first measuring signal processing unit is designed for evaluating these signals. An arrangement for the lesion of heart tissue to treat tachyarrythmias is additionally provided with a stimulation pulse generator, which can be linked via the switching elements to the energy transmission lines and thus to the electrodes by using the program control means. With such a laser ablation device, it is possible in principle to use at the same time for observing the tissue or for the optical detection of measured values by means of fiber optics for coupling the laser energy into the tissue.

In these embodiments, the program control is used to simplify not only the therapy sequence, but also the associated detection of measured values and, if necessary, any preceding stimulation, which makes it even easier for the physician to operate this device.

The above-mentioned means for influencing the ablation program comprise in particular a plurality of additional sensors (respectively associated with the energy uncoupling elements), in particular temperature sensors, a measuring signal processing unit adapted to these sensors and a memory access control connected to the processing unit output for varying the rate and/or sequence of access to the memory regions of the ablation program memory in dependence on the measuring signals and the evaluation result.

In order to further simplify the arrangement, a multiplexer is assigned to the sensors, which is controlled by the program control means in dependence of the ablation program and is designed for transmitting sensor signals via a lower number of sensor transmission lines, as compared to the number of sensors. The safety requirements posed to a program-controlled arrangement of the above sketched type are met in that the program control means have at least one switch-off timer, preferably two, for a safety shutdown of all energy transmission lines if one or several predetermined shutdown criteria are met.

Owing to the fact that the program control means and the switching elements for one advantageous embodiment of the invention are housed in a separate switching device, which is connected on the input side with a traditional ablation device via two serial data lines, a current supply line and a first section of the energy transmission line, a modern arrangement with high use value can be configured from existing ablation devices and catheters by adding components, designed according to the invention, for a retrofitting with little additional expenditure. A step-by-step expansion of new devices is also possible in this way. However, the integrated design in one device is preferred on the whole.

BRIEF DESCRIPTION OF THE DRAWINGS

Advantageous modifications of the invention are otherwise characterized in the dependent claims or are shown in further detail in the following with the aid of the figures and together with the description of the preferred embodiment of the invention, wherein:

DETAILED DESCRIPTION OF THE INVENTION

Figure 1:
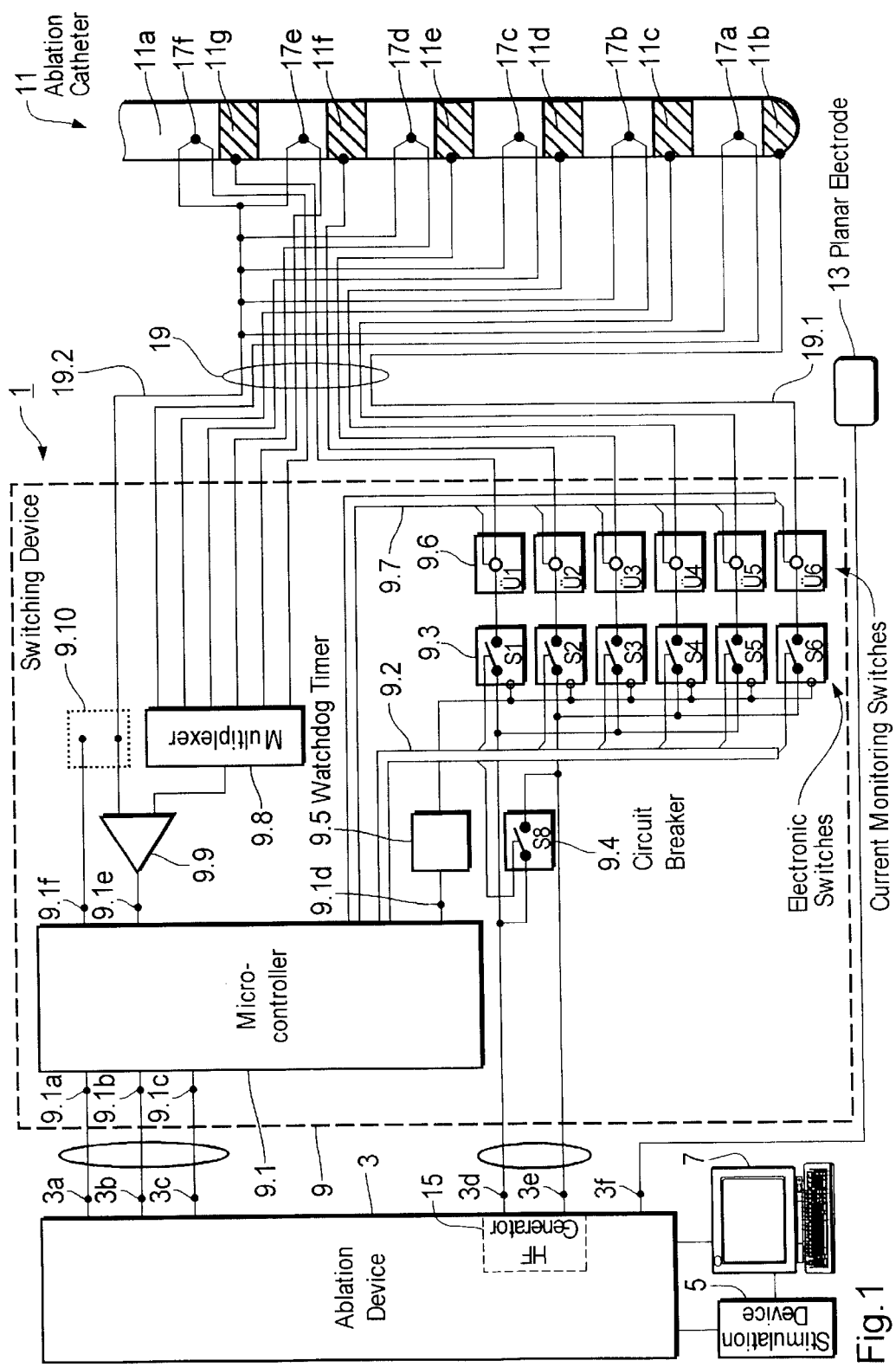
FIG. 1 Shows a block diagram of an ablation arrangement according to a preferred embodiment of the invention.

The ablation arrangement 1, shown in FIG. 1, comprises the following components: ablation device 3, stimulation device 5, clinical measuring location 7, switching device 9, multipolar ablation catheter 11 and planar electrode 13, which all operate jointly in the known manner. The ablation device 3, the HF generator 15 and the output connections are of particular interest to explain the invention. There are two serial data ports 3a, 3b, a power supply connection 3c, an HF power output 3d, 3e and a reference connection 3f for the planar electrode 13.

The ablation catheter 11 itself has a design that is known per se. On an insulating catheter body 11a, made from a biocompatible plastic, the catheter comprises five ring electrodes 11c to 11g in addition to a point electrode 11b. These electrodes are arranged equidistant to each other or to the point electrode and are preferably made from platinum or a Pt—Ir alloy, in the same way as the point electrode 11b. The catheter body 11a contains feed lines (not designated individually) for the individual electrodes, as well as the constantan or copper wires—these are also not designated individually—for the thermo-elements 17a to 17f that are spatially assigned to the electrodes. In one connecting line 19, HF lines 19.1 and the temperature signal lines 19.2 are conducted from the switching device 9 to the ablation catheter 11.

The switching device is connected on the input side to the output connections 3a–3e of the ablation device (via lines that are again not specially designated). The most important components of the switching device 9 include a microcontroller 9.1, six electronic switches 9.3 for the catheter electrodes 11b to 11g that are connected via bus line 9.2 to the microcontroller, as well as a circuit breaker 9.4 and finally a watchdog timer 9.5. Current monitoring sensors 9.6 are assigned to the HF output lines 19.1 and are connected via a second bus line 9.7 to the microcontroller 9.1.

The microcontroller is connected via data inputs and data outputs 9.1a; 9.1b to the data inputs and data outputs 3a, 3b of the ablation device and via a current supply input 9.1c to its current supply output 3c. A separate control output 9.1d is provided for the watchdog timer 9.5.

The Cu lines of the thermal elements 17a to 17f are connected via a multiplexer 9.8, and the constantan line is connected directly to a single measuring amplifier 9.9, the output of which is connected to a first T-signal input 9.1e of the microcontroller. A cold solder joint 9.10, serving as reference, with thermistor (not shown here) for the T acquisition, is connected directly to a second T signal input 9.1f of the microcontroller.

The primary control functions for an ablation treatment (electrode selection and electrode actuation sequence, duration and intervals for the HF pulses, etc.) are preformed in the ablation device 3 (in practical operations also referred to as "ablator" or "ablation system"), following analysis of the results of the clinical examination, obtained with the aid of the measuring location 7, on the basis of a corresponding programming by the physician. Control commands of the ablation device are transmitted via the data outputs 3a, 3b to the microcontroller 9.1, which converts among other things the control commands into control signals for the switches 9.3 and the multiplexer 9.9, monitors the switching functions by means of the current sensors 9.6 and calculates the temperature at the individual electrodes 17a to 17f.

The switching arrangement as shown permits the release of HF energy with each optional ring-electrode combination (including combinations with the surface electrode or neutral electrode 13), as well as the application of stimulation pulses and the detection of the intracardiac electrogram IEGM at the respectively connected electrodes. Owing to a synchronous control of the multiplexer 9.8, the temperature at the electrodes can be monitored at the same time. However, if necessary, the multiplexer can also be controlled asynchronous to the switches. The results of the T monitoring are transmitted to the ablation device 3 to be displayed for the physician and for a possible modification of the ablation program. However, they can also be used internally in the microcontroller 9.1 to trigger an electrode shutdown in case of unacceptably high T values.

The switches 9.3 and 9.4 are preferably designed as MOSFET switches, but can also be in the form of relays, in particular, if the switching speed limitation based on the principle is acceptable. The bidirectional data transfer between ablation device 3 and switching device 9 or a corresponding programming of the ablation device permit a short-term scanning of the HF for each electrode switching in order to reduce the stress on the switch. This is particularly advantageous when using relays.

With another embodiment of the invention—not shown here—one or several IEGM and/or stimulation channels may be connected between the switches 9.3 and the monitoring elements 9.6 so that the same can be coupled in or coupled out and thus also treated independent of the switches 9.3 for the HF path.

Figure 2:
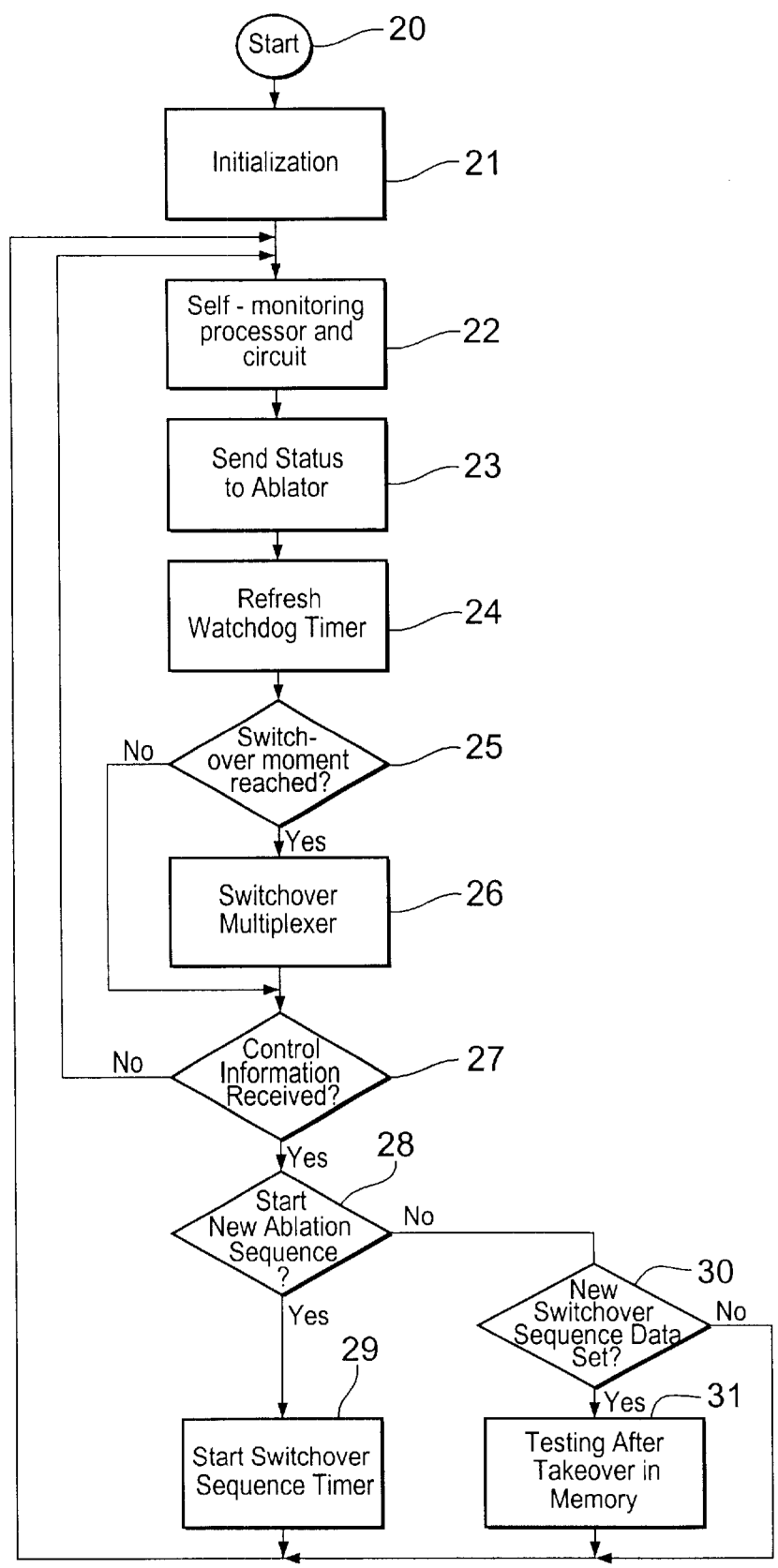
FIG. 2 Shows as a detailed view of FIG. 1 a flow diagram for the functional representation of a software-controlled program control unit, and FIG. 3 Shows as a different embodiment an operational block diagram of essential components of another program control unit according to FIG. 1, close to a hardware representation.

The flow diagram shown in FIG. 2 illustrates a possible embodiment of a control program for the microcontroller 9.1 according to FIG. 1, in the form of a program flow chart.

With the illustrated program sequence for the microcontroller forming the system controller, it can be seen that this software is divided into those sections which are kept resident in the program memory of microcontroller 9.1 and those sections that can be loaded optionally into the microcontroller prior to ablation.

The program steps to be carried out by the microcontroller in this case result from the sequence shown in FIG. 2: following start-up (activation marker 20), the microcontroller successively performs an initialization (step 21), carries out an automatic test via a self-monitoring processor and circuit, (step 22) and triggers the return to an initial state or sends a status signal to the ablator (step 23). The program memory in this case is located in step 22, together with the processor.

The "ablation program" in this case forms an ablation sequence consisting of a succession of switching sequences, which differ with respect to time sequence and number. While the start of the ablation sequence is determined by the physician by issuing a control command for starting the ablation sequence, the time sequence and the number of switching sequences—starting with a basic program—are variable and can be changed based on the signals received from the ablation device.

The watchdog timer (step 24) sets the switching moments within the sequence. Once the interval for an ablation period is completed or a switchover moment is reached (decision step 25), the multiplexer (step 26) is switched and the following electrode is triggered by the HF generator. In the other case, the present switching state is maintained. If a control information for changing the program sequence (temperature or external control) has been received in the meantime (decision step 27), a decision is made during the following decision step 28 whether the control information initiates a new ablation sequence. Otherwise, there is a jump back to before the initialization step 21 and the switching sequence starts again, based on the steps taken so far.

If a control information concerning the start of a new ablation sequence is received, this sequence is triggered via the step 29 by issuing a corresponding signal to the step 22 and thus the initiation of the new switchover sequence begins. If a decision is made in the following decision step 28 that this was not a start signal, it is assumed that a new switching sequence data record exists. This is checked in decision step 30 and takeover into the memory (step 22) is triggered in step 31, provided the check in decision step 30 was successful. Otherwise, the memory from step 22 is admitted with the unchanged signal. In that case, the microcontroller processes program sections for securing the system and waits for control information from the ablation device. Such control information concerns data records with information on the ring selection or information for starting or stopping an ablation sequence. In that case, the controller serially converts data records received from the ablation device into switching information, which changes the ablation program. In FIG. 1, the microcontroller is connected for this to the ablation device 3 via the connections 3a to c.

Figure 3:
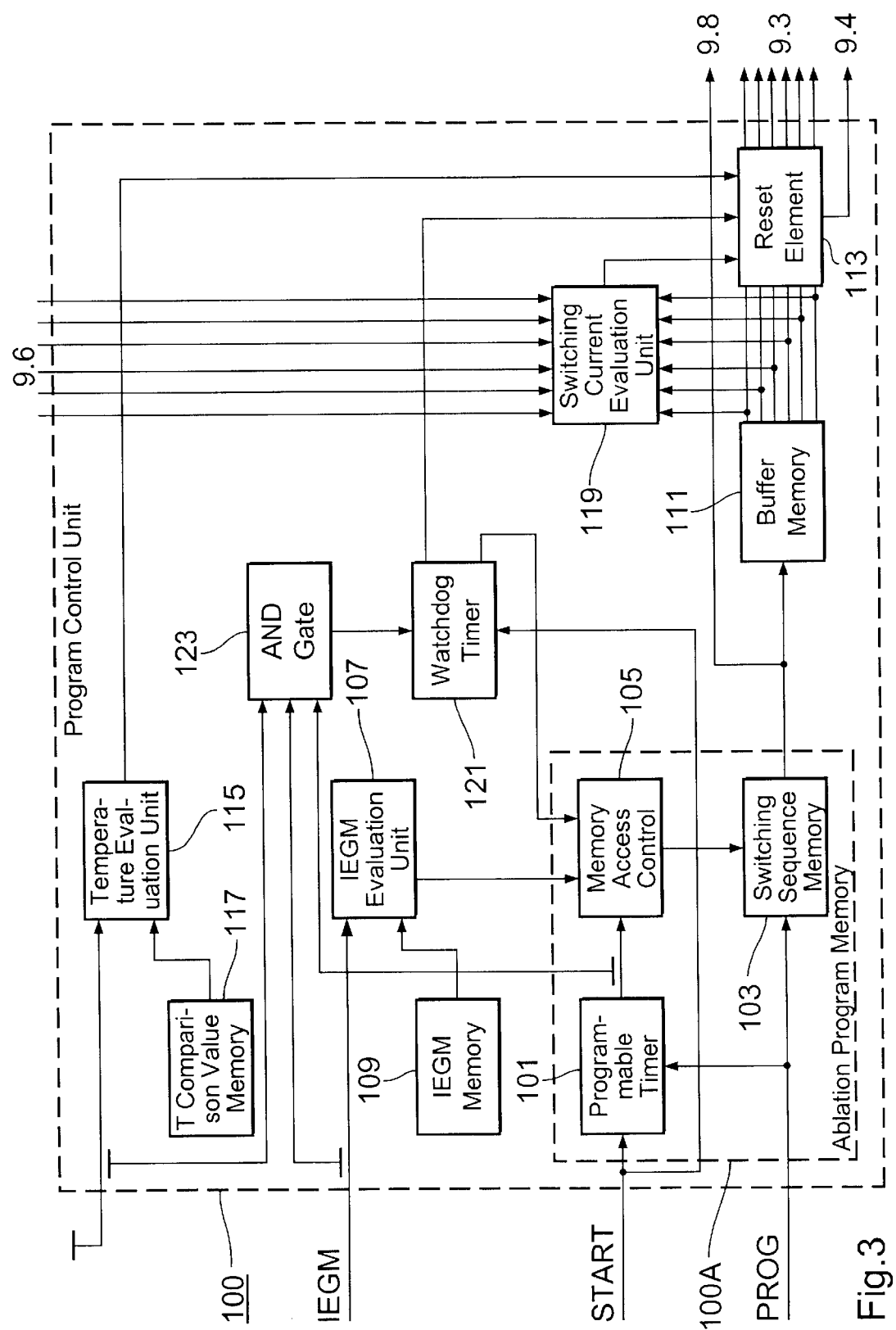

Another hardware-type realization in the form of a basic wiring diagram is shown in FIG. 3, a preferred embodiment of the essential components of the program control unit 100 according to the invention. As a practical embodiment, it can be formed by components of a known ablation device and an additional switching device (see diagram in FIG. 1) or represent a component of a new type of ablation device.

As an essential operational group, the program control unit 100 comprises first of all a programmable timer 101, a switching sequence memory 103 and a memory access control 105, which is assigned to the switching sequence memory and is connected on the input side to the timer 101. Together, these form an ablation program memory 100A.

The memory access control 105 is also connected on the input side to an IEGM evaluation unit 107, one input of which is supplied by a IEGM signal processing unit (not shown in the Figure) with the respectively current IEGM, recorded via the active electrode of the ablation catheter, while the second input is connected to an IEGM memory 109. The output of switching sequence memory 103 in this case is connected to a buffer memory or a switching position hold element 111. At the output of this element, an activation signal related to the switch 9.3 (FIG. 1) is respectively available, which is symbolized in the FIG. 3 by showing a number of outputs that correspond to the switching number. Furthermore, the output of the switching sequence memory is connected to the multiplexer 9.8 (FIG. 1), assigned to the T-sensors 17a to 17f, and activates this multiplexer based on the current activation signal for the electrodes.

On the output side, a reset element 113 is assigned to the switching position hold element 111, which is in turn connected on the output side to the electrode switches 9.3, as well as additionally to the HF feed switch 9.4. The reset element 113 is connected at one control input to the output of a temperature evaluation unit 115, which in turn is fed via an input the temperature value T at the currently triggered electrode and which is connected via a second input to a T comparison value memory 117. Another control input of the reset element 113 is connected to a switching current evaluation unit 119, which in turn is connected on the input side to the current monitoring sensors 9.6 (FIG. 1), as well as the switching position memory 111. Finally, the reset element is connected via a third control input, which has an OR relation to the two other inputs, to the output of a watchdog timer 121. On the input side, not specifically designated detection means for detecting a regular transmission of the IEGM and T data to the program control unit, as well as a transmission of timer signals to the memory access control 105 are connected to this watchdog timer via an AND gate 123.

As a result of the evaluation of the clinical finding and adjusted to the catheter used in the concrete or actual case, a programming of the ablation memory 100A, the timer 101 and the switching sequence memory 103—symbolized in the FIG. 3 by the signal "PROG"—is carried out prior to each treatment. With this programming, a basic ablation program is fixed, which determines the switching sequence and duration of the activation of the individual ablation electrodes.

Following a "START" signal, the treatment is initiated according to this program in that the first switch position is read out of the switching sequence memory 103 via the timer 101 and the memory access control 105, and is then stored in the buffer memory 111. The initially selected switch 9.3 is then first activated and the associated T-sensor is selected via the multiplexer 9.8. The selected electrode remains switched on for the preprogrammed time interval.

Subsequently, the next electrode provided in the ablation program is connected to the HF generator, provided the physician does not initiate a modification of the basic program due to special circumstances.

Such a modification can occur at the catheter as a result of detecting excessive temperature values by resetting the respective switch 9.3 via the resetting element 113, which is controlled via the temperature evaluation unit 115. The watchdog timer 121 furthermore activates the resetting element, thus shutting down the complete HF or the individual electrode feed lines if irregularities in the data transmission are detected. An analog shutdown finally occurs, which is controlled via the switch current evaluation unit 119, if a current is detected on an electrode feed line other than the one connected to the HF generator according to the program.

A delay in the switching sequence is effected by the IEGM evaluation unit 107 via the memory access control 105 if the local electrogram, detected during the ablation, at the location of the activated electrode does not correspond to a predetermined comparison pattern during the course of the programmed start-up time. This is an indication that a removal of tissue has not yet occurred. The evaluations necessary for such a control operation are relatively complex.

One simplified variant—a variant not shown in further detail—provides that in place of the modules 107 and 109, the physician has the option of intervening by using corresponding actuation elements, which results in an extension of the time the HF is effective, as compared to the basic ablation program, by observing the IEGM signal and through a manual switching. For this, a different suitable program sequence is recorded in the memory via suitable input means. An exchange of the program data in this case preferably can occur through reading in corresponding software from a data carrier. In one preferred embodiment, the program control means according to the invention are provided in a PC or a laptop.

Otherwise, the design of the invention is not limited to the aforementioned preferred embodiments. Rather, a number of variants are possible, which make use of the presented solution, even in a different type of embodiment.

Thus, in place of the above-mentioned thermal elements, thermistors can also be provided in the ablation catheter and their number must not be equal to the number of electrodes. Furthermore, it is also possible to use the detection of excessively low temperatures as a trigger for control functions in addition to registering excessively high temperatures, particularly for an extension of the electrode operating time. For one simple embodiment of the arrangement, it is possible to omit the T monitoring completely.

The total system can operate completely with PC control and the above-addressed control system functions can for the most part be realized with software (even independent of a PC configuration).

What is claimed is:

1. An ablation arrangement for the targeted production of local lesions in living tissue inside a body, comprising:
   at least one energy source;
   a holding element;
   a plurality of energy uncoupling elements mounted on the holding element;
   a plurality of energy transmission lines, each energy transmission line connecting the at least one energy source to a respective one of the energy uncoupling elements;
   switching elements associated with the energy transmission lines for one of making and interrupting a connection between the at least one energy source and each respective energy uncoupling element; and
   program control means, including a program memory storing a control program, for providing a time dependent actuation of at least some of the switching elements according to the control program wherein the control program is influenced by at least one variable thereby changing the time dependent actuation of the remaining switching elements to obtain a timed sequence of ablation pulses via the energy uncoupling elements.

2. An ablation arrangement according to claim 1, wherein the program memory is a read/write memory for recording different programs.

3. An ablation arrangement according to claim 1, further including means for changing a stored basic ablation program in dependence on at least one variable that is input prior to or during the treatment and/or measured during the treatment.

4. An ablation arrangement according to claim 1, wherein the energy source comprises an HF power source (15), the holding element as comprises a catheter body, the energy uncoupling elements comprise electrodes, the energy transmission lines comprise electrical lines (19.1) and the switching elements comprise electromechanical or electronic switches.

5. An ablation arrangement according to claim 1, wherein the energy source comprises a high-powered radiation source, the holding element comprises a catheter body, the energy transmission lines and the energy uncoupling elements comprise a waveguide arrangement and the switching elements comprise electro-optical switching elements.

6. An ablation arrangement according to claim 5, wherein the energy uncoupling elements further comprise electrodes, and further comprising a stimulation pulse generator connectable to one of the electrodes at least for certain periods of time via at least one of the switching elements and at least one of the transmission lines in dependence on an output signal from the program control means.

7. An ablation arrangement according to claim 5, wherein the energy uncoupling elements further comprise electrodes arranged for recording intracardiac electrogram signals (IEGM) or monophase action potentials and further comprising a first measuring signal processing unit for evaluating said signals.

8. An ablation arrangement according to claim 5, wherein the high-powered radiation source is a laser.

9. An ablation arrangement according to claim 1, wherein the energy uncoupling elements simultaneously function as first sensors and further comprising a first measuring signal processing unit for evaluating recorded measured signals connectable to the energy transmission lines, wherein the individual energy uncoupling elements are connectable at least during some time intervals to the input of the first measuring signal processing unit under control of the program control means.

10. An ablation arrangement according to claim 9, wherein the energy uncoupling elements comprise electrodes arranged for recording intracardiac electrogram signals (IEGM) or monophase action potentials and the first measuring signal processing unit is for evaluating said signals.

11. An ablation arrangement according to claim 9, and further comprising means for influencing the control program including a plurality of second sensors assigned to the energy uncoupling elements, a second measuring signal processing unit and switching means connected to an output of the second measuring signal processing unit for changing the control program in dependence on the signals detected with the second sensors.

12. An ablation arrangement according to claim 11, further comprising a multiplexer assigned to the second sensors and controlled by the program control means (9.1; 100) in dependence on the control program, for picking up the sensor signals via measuring signal transmission lines or connections (9.1e; 9.1f), the number of which is lower as compared to the number of sensors.

13. An ablation arrangement according to claim 11, wherein the plurality of second sensors are temperature sensors.

14. An ablation arrangement according to claim 9, wherein the energy uncoupling elements further comprise electrodes, and further comprising a stimulation pulse generator connectable to one of the electrodes at least for certain periods of time via at least one of the switching elements and at least one of the transmission lines in dependence on an output signal from the program control means.

15. An ablation arrangement according to claim 1, wherein the at least one energy source comprises a single energy source.

16. An ablation arrangement according to claim 1, wherein the program control means includes at least one shutdown timer which functions as a safety shutoff for all energy transmission lines in dependence of predetermined shutdown conditions.

17. An ablation arrangement according to claim 1, wherein the program control means and the switching elements are housed in one of a separate switching device and a switching device that is integrated into a basic device, which is connected on an input side via two serial data lines, one current supply line and one energy transmission line section to an ablation device.

18. An ablation arrangement according to claim 1, wherein the body is a heart.

* * * * *